US009045097B2

(12) United States Patent
Yamada et al.

(10) Patent No.: US 9,045,097 B2
(45) Date of Patent: Jun. 2, 2015

(54) TWO-DIMENSIONAL POSITION MAP CORRECTING METHOD

(75) Inventors: Yoshihiro Yamada, Kyoto (JP); Tomoaki Tsuda, Kyoto (JP); Masanobu Sato, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 187 days.

(21) Appl. No.: 13/703,303

(22) PCT Filed: Feb. 7, 2011

(86) PCT No.: PCT/JP2011/000662
§ 371 (c)(1),
(2), (4) Date: Dec. 10, 2012

(87) PCT Pub. No.: WO2011/155103
PCT Pub. Date: Dec. 15, 2011

(65) Prior Publication Data
US 2013/0077848 A1 Mar. 28, 2013

(30) Foreign Application Priority Data
Jun. 10, 2010 (JP) .................................. 2010-133065

(51) Int. Cl.
*G06K 9/00* (2006.01)
*B60R 16/033* (2006.01)
*B60K 6/445* (2007.10)
(Continued)

(52) U.S. Cl.
CPC ............... *B60R 16/033* (2013.01); *B60K 6/445* (2013.01); *B60W 10/06* (2013.01);
(Continued)

(58) Field of Classification Search
None
See application file for complete search history.

(56) References Cited

U.S. PATENT DOCUMENTS 7,026,621 B2 * 4/2006 Stonger et al. ........... 250/363.03
(Continued)

FOREIGN PATENT DOCUMENTS

JP   11-142524 A     5/1999
JP   2005-043104 A   2/2005
WO   WO-2009/116174 A1   9/2009

OTHER PUBLICATIONS

International Search Report issued in International Patent Application No. PCT/JP2011/000662 dated Mar. 24, 2011.

*Primary Examiner* — Matthew Bella
*Assistant Examiner* — Jason Heidemann
(74) *Attorney, Agent, or Firm* — McDermott Will & Emery LLP

(57) ABSTRACT

Even when areas delimited by delimiting points are not appropriate and area division has failed, success or failure of area division in such areas can easily be determined by applying a map determination condition in the map determining step (step S50). And since the areas delimited by the delimiting points are changed and the map determining step (step S50), including also steps S22 and S23 and steps S30 and S40, is repeated until the map determination condition is satisfied, the areas satisfying the map determination condition are determined appropriate and the area division in such areas can be carried out accurately. Even when there is distortion, a two-dimensional position map can be corrected accurately.

24 Claims, 7 Drawing Sheets

(51) Int. Cl.
*B60W 10/06* (2006.01)
*B60W 10/26* (2006.01)
*B60W 20/00* (2006.01)
*G01T 1/20* (2006.01)
*G06T 7/00* (2006.01)
*G01T 1/164* (2006.01)

(52) U.S. Cl.
CPC ............... *B60W 10/26* (2013.01); *B60W 20/00* (2013.01); *B60W 2710/0644* (2013.01); *B60W 2710/0666* (2013.01); *B60Y 2300/92* (2013.01); *Y02T 10/6239* (2013.01); *G01T 1/20* (2013.01); *G06T 7/0012* (2013.01); *G01T 1/1644* (2013.01)

(56) References Cited

U.S. PATENT DOCUMENTS

| | | | |
|---|---|---|---|
| 8,278,625 B2* | 10/2012 | Sato et al. | 250/362 |
| 8,471,211 B2* | 6/2013 | Yamada et al. | 250/363.09 |
| 8,750,569 B2* | 6/2014 | Laurence et al. | 382/103 |
| 8,787,620 B2* | 7/2014 | Laurence et al. | 382/103 |
| 8,809,793 B2* | 8/2014 | Wagadarikar et al. | 250/363.04 |
| 2005/0061983 A1* | 3/2005 | Stonger et al. | 250/363.03 |
| 2010/0327168 A1* | 12/2010 | Yamada et al. | 250/362 |
| 2011/0001050 A1 | 1/2011 | Sato et al. | |

* cited by examiner

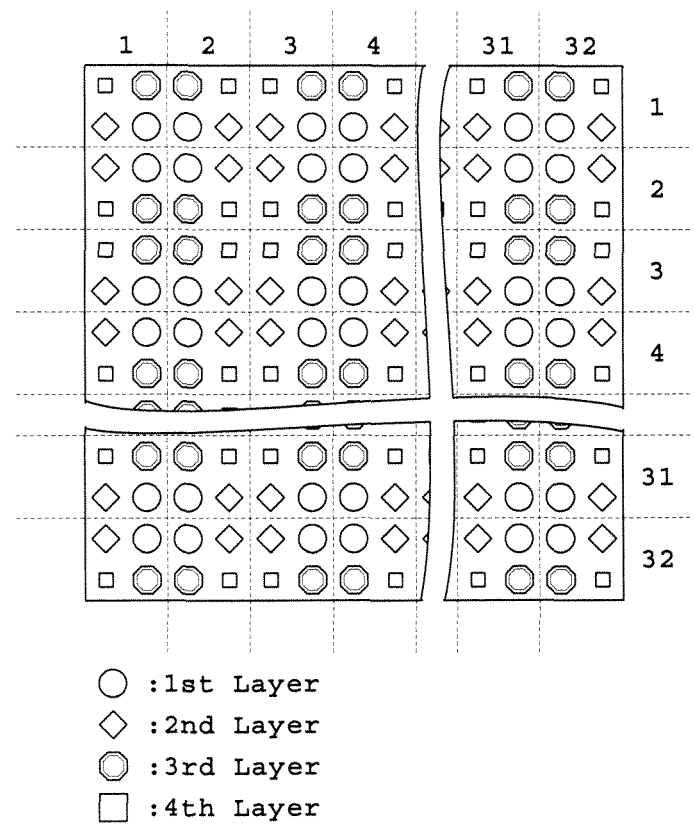

TWO-DIMENSIONAL POSITION MAP CORRECTING METHOD

RELATED APPLICATIONS

This application is the U.S. National Phase under 35 U.S.C. §371 of International Application No. PCT/JP2011/000662, filed on Feb. 7, 2011, which was published as WO2011/155103 on Dec. 15, 2011, which claims priority from Japanese Patent Application No. 2010-133065 filed Jun. 10, 2010. The subject matter of each is incorporated herein by reference in entirety.

TECHNICAL FIELD

This invention relates to a two-dimensional position map correcting method for correcting a two-dimensional position map used when detecting radiation with radiation detectors each including a plurality of scintillator elements and a light sensor optically connected thereto.

BACKGROUND ART

A PET (Positron Emission Tomography) apparatus will be described as an example of nuclear medicine diagnostic apparatus, i.e. ECT (Emission Computed Tomography) apparatus. The PET apparatus is constructed to detect a plurality of γ-rays generated by annihilation of positrons, and to reconstruct a sectional image of a patient only when a plurality of detectors simultaneously detect the γ-rays.

Specifically, a patient is medicated with a radioactive drug including a positron-emitting radionuclide, and detectors consisting of numerous detecting element (e.g. scintillator) groups detect pair annihilation γ-rays of 511KeV released from the patient medicated. And when two detectors detect γ-rays within a definite period of time, they are counted as one pair of annihilation γ-rays detected as a coincidence, and a pair annihilation generating point is determined to exist on a straight line linking the detector pair having detected them. Such coincidence information is accumulated and reconstruction is carried out to obtain a positron-emitting radionuclide distribution image (i.e. a sectional image).

At this time, image resolution of the sectional image is improved by discriminating not only γ-ray detecting positions (γ-ray incident positions) on the detectors but γ-ray detecting positions on the scintillators as more particular γ-ray detecting positions, to increase γ-ray detecting accuracy. So, the number of scintillators is increased to increase discriminating capability. In recent years, in particular, DOI detectors have been developed, which have scintillators laminated also in a depth direction to be capable of discriminating light source positions having caused interaction in the depth direction (DOI: Depth of Interaction).

To discriminate γ-ray incident positions, a two-dimensional position map prepared beforehand is used. The two-dimensional position map is a map showing, in two dimensions, the number of luminescent photons (corresponding to a count value of γ-rays) obtained with light sensors represented by photomultiplier tubes (PMT), as corresponding to incident positions of γ-rays incident on the scintillators. FIG. 10 shows a two-dimensional position map in the case of a DOI detector having four layers of scintillators laminated in the depth direction. The positions indicated by white circles (shown as "○" in FIG. 10) are scintillators in the first layer (written "1st Layer" in FIG. 10). The positions indicated by white rhombuses are scintillators in the second layer (written "2nd Layer" in FIG. 10). The positions indicated by white double octagons are scintillators in the third layer (written "3rd Layer" in FIG. 10). The positions indicated by white rectangles (shown as "□" in FIG. 10) are scintillators in the fourth layer (written "4th Layer" in FIG. 10). Incident positions of actually incident γ-rays can be discriminated by referring to a look-up table (LUT) having each position in the two-dimensional position map corresponding to each scintillator, and referring to the two-dimensional position map.

Incidentally, where a plurality of scintillators are arranged in three dimensions as in the DOI detector, diffusion is provided by combination of a light reflective material and a light transmissive material, for example, between adjoining scintillators, so that positions do not overlap in the two-dimensional position map. Further, a technique of correcting the two-dimensional position map has been introduced, which carries out a statistical clustering process in order to increase the discriminating capability still further (see Patent Document 1, for example).

In order to prepare a map accurately also when this two-dimensional position map has a large distortion, Inventors herein have proposed a technique of partly preparing a histogram from the map and constructing a map successively from a portion of clear peak toward end portions (see Patent Document 2, for example).

[Patent Document 1]
Unexamined Patent Publication No. 2005-43104
[Patent Document 2]
International Publication No. WO2009-116174

DISCLOSURE OF THE INVENTION

Problem to be Solved by the Invention

However, the scintillator elements of the DOI detector become numerous, and the number of areas corresponding to the scintillator elements increases on the two-dimensional position map. Therefore, in Patent Document 1 noted above, a presumption in the statistical clustering process will take time. When peak detection is carried out on the two-dimensional position map for area division, the accuracy of detecting a peak position worsens due to the problem of statistical accuracy of the two-dimensional position map. When division is carried out by adding count values of the entire two-dimensional position map, to partition it into a grid form, and the two-dimensional position map has distortion, the areas cannot be divided accurately. Further, since the number of areas on the two-dimensional position map is huge, when the areas are manually divided, the operation will consume a very long time.

So, as in Patent Document 2 noted above, a discriminating method has been devised to enable area division also when an arrangement of areas corresponding to the scintillator elements has distortion, by making a two-dimensional position map into histograms gradually from the whole to parts, and searching and finding delimiting points. However, when the distortion of the arrangement of areas corresponding to the scintillator elements is large, even the technique of the above Patent Document 2 may fail to divide the areas accurately. In addition to the necessity to determine, with the naked eye, a success or failure in the area division, a time-consuming operation is needed to move area boundaries manually after a determination is made to be a failure.

This invention has been made having regard to the state of the art noted above, and its object is to provide a two-dimensional position map correcting method which can correct a two-dimensional position map accurately even when there is distortion.

Means for Solving the Problem

To fulfill the above object, this invention provides the following construction.

A two-dimensional position map correcting method of this invention is used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising a histogram preparing step for acquiring a histogram by preparing the histogram with a vertical axis representing signal strengths of the two-dimensional position map and with a horizontal axis being in a coordinate axis direction of the two-dimensional position map; and a map determining step for applying a map determination condition using amounts of characteristic extracted from grid shapes delimited vertically and horizontally on the two-dimensional position map, to areas delimited by delimiting points based on the histogram acquired in the histogram preparing step; the map determining step being repeated until the map determination condition is satisfied, by changing the areas delimited by the delimiting points.

[Functions and effects] According to the two-dimensional position map correcting method of this invention, a histogram preparing step is provided for acquiring a histogram by preparing the histogram with a vertical axis representing signal strengths of the two-dimensional position map and with a horizontal axis being in a coordinate axis direction of the two-dimensional position map. A map determining step is provided for applying a map determination condition using amounts of characteristic extracted from grid shapes delimited vertically and horizontally on the two-dimensional position map, to areas delimited by delimiting points based on the histogram acquired in the histogram preparing step. Even when the areas delimited by the delimiting points are not appropriate and the area division has failed, a success or failure of area division in such areas can easily be determined by applying the map determination condition in the map determining step. And since the areas delimited by the delimiting points are changed and the map determining step is repeated until the map determination condition is satisfied, the areas satisfying the map determination condition are determined appropriate and the area division in such areas can be carried out accurately. Even when there is distortion, the two-dimensional position map can be corrected accurately.

The histogram preparing step, in a specific example thereof, is executed to obtain totals of the signal strengths along a coordinate axis of the two-dimensional position map, and acquire the above histogram by preparing the histogram with a vertical axis representing the totals of the signal strengths and with a horizontal axis being in a coordinate axis perpendicular to that coordinate axis.

In a specific example of the two-dimensional position map correcting method of this invention, the map determining step is repeated by applying the above map determination condition to the areas delimited by the delimiting points, and changing the areas delimited by the delimiting points in the order of large total of the signal strengths until the map determination condition is satisfied. Normally, areas with large totals of the signal strengths are regarded as appropriate. When the map determination condition is not satisfied, the areas concerned are regarded as inappropriate, and the areas are changed in the order of large total of the signal strengths, and the map determining step is repeated, whereby an area with the largest total of the signal strengths can be found among the areas regarded as appropriate.

The correction may be stopped when the number of times of repeating the map determining step exceeds a preset number of times. The correction may be stopped when the areas delimited by the delimiting point no longer exist in the map determining step. Through such determination, a failure in dividing the areas can be determined automatically.

Preferably, the following determination is made in order to find the above delimiting points. That is, a delimiting point determining step is provided for comparing the respective signal strengths of the histogram, and obtaining local minimum values, respectively, thereby to determine positions of the local minimum values to be the delimiting points. By obtaining the local minimum values, the respective delimiting points can be determined accurately.

The delimiting point determining step may be a delimiting reference point determining step for determining delimiting points serving as references to be reference delimiting points. The delimiting point determining step may include a provisional delimiting reference point determining step for determining delimiting points serving as provisional references to be provisional reference delimiting points; and a delimiting reference point determining step for comparing the respective signal strengths in the areas divided at the provisional delimiting reference points determined in the provisional delimiting reference point determining step, and obtaining the local minimum values, respectively, thereby to determine positions of these local minimum values to be reference delimiting points which are delimiting points serving as references. That is, in the former case, the reference delimiting points are determined without determining the provisional delimiting reference points. In the latter case, the reference delimiting points are determined after determining the provisional delimiting reference points.

Preferably, a delimiting point altering step is provided for altering the positions of the delimiting points to be altered, based on the delimiting reference points determined in the above delimiting reference point determining step, by comparing respective signal strengths around the delimiting points to be altered; wherein, after alterations made in the delimiting point altering step, the map determination condition is applied. With this alteration of the delimiting points, the altered delimiting points have distortion taken into account, and the areas delimited by the delimiting points will also become accurate.

Preferably, a delimiting point re-altering step is provided for re-altering the positions of the delimiting points by comparing the respective delimiting points altered in the above delimiting point altering step; wherein, after re-alterations made in the delimiting point re-altering step, the map determination condition is applied. With this re-alteration of the delimiting points, the re-altered delimiting points have distortion taken into account still further, and the areas delimited by the delimiting points will also become still more accurate.

One example of the map determination condition is that a ratio between an average width at one end and an average width at the other end of the grid delimited at the delimiting points is a predetermined ratio or less. If the ratio between the average widths exceeds the predetermined ratio, it can be considered that the difference in width between the ends has increased, and thus these areas can be determined inappropriate. Conversely, if the ratio between the average widths is the predetermined ratio or less, it can be considered that there is little difference in width between the ends, and thus these areas can be determined appropriate.

Another example of the map determination condition is that grids with horizontal to vertical ratios of the width of the grids delimited at the delimiting points deviating from 1 exist in a predetermined number or less. The closer to 1 the horizontal to vertical ratio of the width of the grid is, the closer the grid is to a square. Conversely, the farther it deviates from 1, the farther away the grid is from a square. Therefore, if grids deviating from 1 exceed the predetermined number, such area can be determined inappropriate. Conversely, if grids deviating from 1 exist in the predetermined number or less, such area can be determined appropriate.

A further example of the map determination condition is that an average size near an end is smaller than an average size in a center of the grid delimited at the delimiting points. When the size near an end of the grid is larger than the size in the center, the grid at the end is squeezed by the grid near the end, and thus such area can be determined inappropriate. Conversely, when the size near the end of the grid is smaller than the size in the center, the grid at the end is not squeezed by the grid near the end, and thus such area can be determined appropriate.

Effects of the Invention

With the two-dimensional position map correcting method according to this invention, even when areas delimited by delimiting points are not appropriate and area division has failed, success or failure of area division in such areas can easily be determined by applying a map determination condition in the map determining step. And since the areas delimited by the delimiting points are changed and the map determining step is repeated until the map determination condition is satisfied, the areas satisfying the map determination condition are determined appropriate and the area division in such areas can be carried out accurately. Even when there is distortion, a two-dimensional position map can be corrected accurately.

BRIEF DESCRIPTION OF THE DRAWINGS

FIG. 10 is a plan view of a two-dimensional position map in the case of a DOI detector having four layers of scintillators laminated in a depth direction.

DESCRIPTION OF REFERENCES

3 . . . γ-ray detectors
31 . . . scintillator block
32 . . . photomultiplier tube (PMT)
$G_1, G_3$ . . . histograms (graphs)
$D_1, D_2$ . . . delimiting reference points
M . . . two-dimensional position map

[Embodiment]

An embodiment of this invention will be described hereinafter with reference to the drawings.

Figure 1:
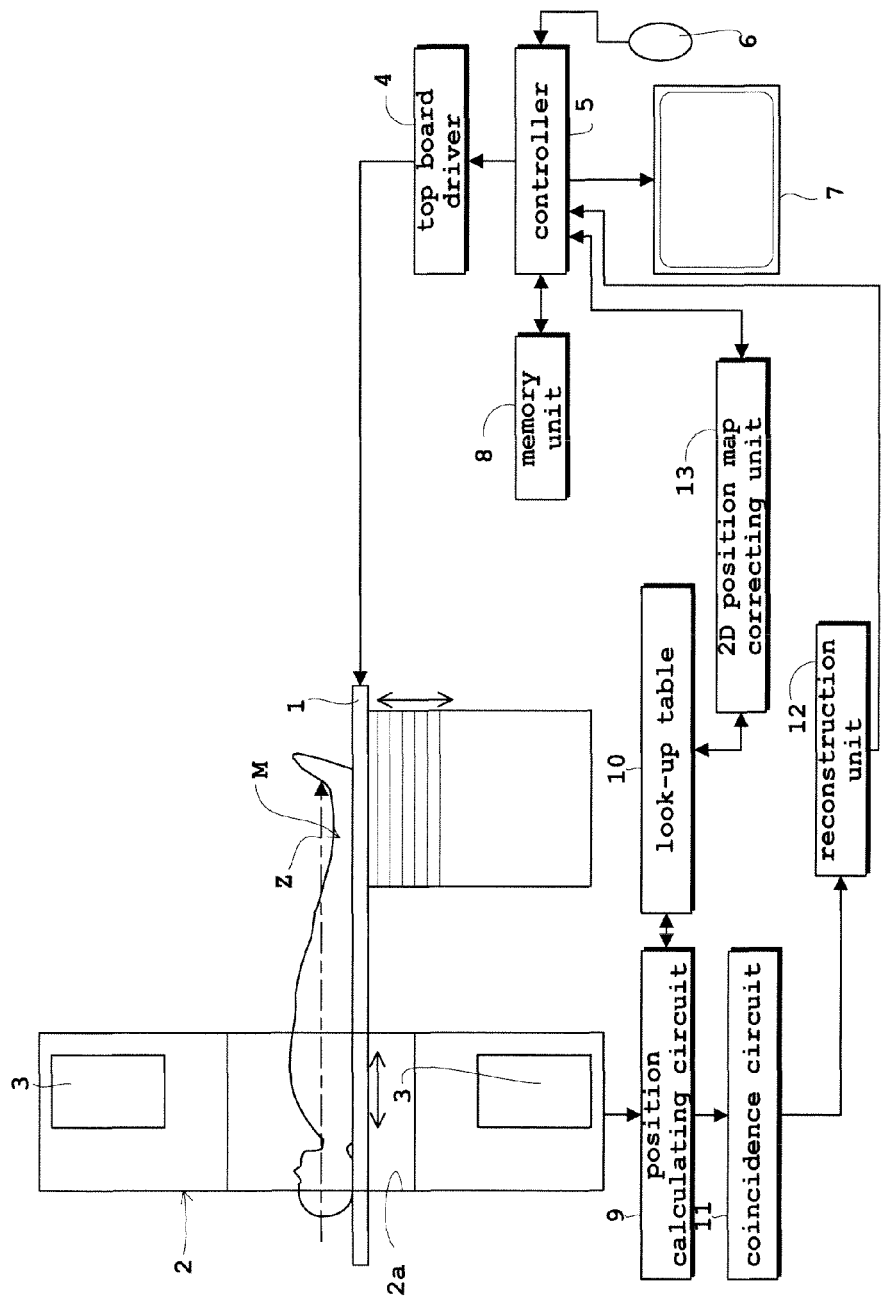
FIG. 1 is a side view and block diagram of a PET (Positron Emission Tomography) apparatus according to an embodiment.
Figure 2:
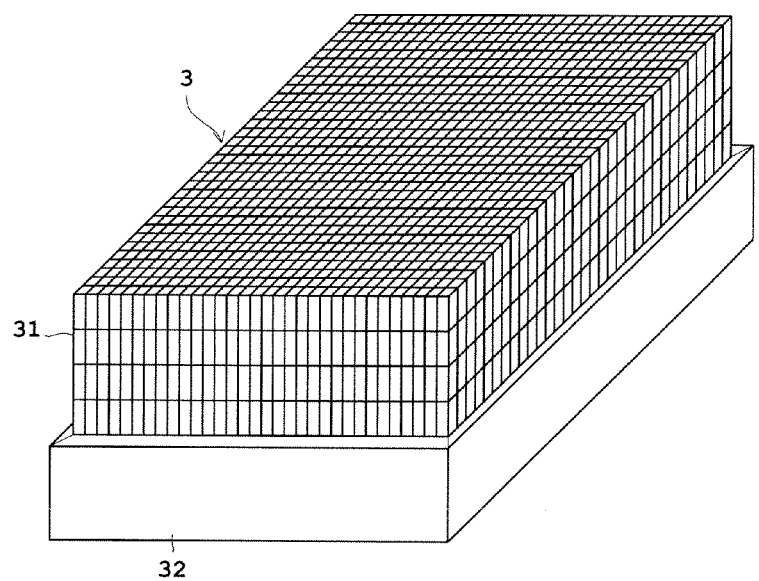
FIG. 2 is a schematic perspective view of a γ-ray detector.
Figure 3:
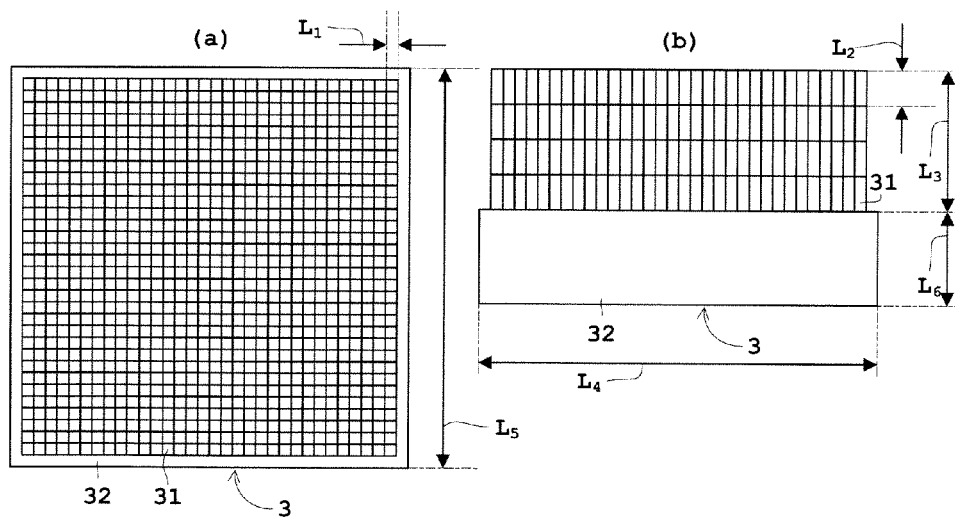
FIG. 3 (a) is a plan view of the γ-ray detector, and (b) is a side view of the γ-ray detector.

FIG. 1 is a side view and block diagram of a PET (Positron Emission Tomography) apparatus according to the embodiment. FIG. 2 is a schematic perspective view of a γ-ray detector. FIG. 3 (a) is a plan view of the γ-ray detector. FIG. 3 (b) is a side view of the γ-ray detector.

The PET apparatus according to this embodiment, as shown in FIG. 1, includes a top board 1 for supporting a patient M. This top board 1 is constructed to move up and down and make parallel translation along the body axis Z of the patient M. With this construction, the patient M placed on the top board 1 passes through an opening 2a of a gantry 2 described hereinafter, to be scanned in order from the head to the abdomen and the feet, to obtain images of the patient M. There is no limitation as to the sites scanned or the scanning sequence of the respective sites.

The PET apparatus according to this embodiment includes the gantry 2 with the opening 2a and γ-ray detectors 3, besides the top board 1. The γ-ray detectors 3 are arranged in a ring form so as to surround the body axis Z of the patient M, and are embedded in the gantry 2. The γ-ray detectors 3 correspond to the radiation detectors in this invention.

In addition, the PET apparatus according to this embodiment includes a top board driver 4, a controller 5, an input unit 6, an output unit 7, a memory unit 8, a position calculating circuit 9, a look-up table 10, a coincidence circuit 11, a reconstruction unit 12 and a two-dimensional position map correcting unit 13. The top board driver 6 is a mechanism for driving the top board 1 to make the above movements, and has a motor not shown.

The controller 5 performs overall control of the components forming the PET apparatus according to this embodiment. The controller 5 includes a central processing unit (CPU) and others.

The input unit 6 feeds the controller 5 with data and commands inputted by the operator. The input unit 6 includes a pointing device represented by a mouse, keyboard, joystick, trackball and/or touch panel. The output unit 7 includes a display unit represented by a monitor, a printer, and so on.

The memory unit 8 and look-up table 10 are formed of storage media represented by a ROM (Read-only Memory), RAM (Random-Access Memory) and the like. In this embodiment, a count of coincidences counted by the coincidence circuit 11 and images processed by the reconstruction unit 12 are written and stored in a RAM, and are read from the RAM as necessary. In this embodiment, in particular, a two-dimensional position map showing, in two dimensions, counts corresponding to signal strengths of electric signals acquired from photomultiplier tubes 33 (see FIGS. 2 and 3) described hereinafter, and made to correspond to incident positions of γ-rays incident on scintillator elements of scintillator blocks 31 (see FIGS. 2 and 3) described hereinafter, is written and stored in the look-up table 10 as a table having each position in the two-dimensional position map and each scintillator element in a corresponding relationship, which is read from the look-up table 10 at a time of correction of the two-dimensional position map by the two-dimensional position map correcting unit 13, and detection signals of γ-rays are made to correspond to crystal elements with reference to the table. In this embodiment, map determination conditions described hereinafter are written and stored beforehand to be applied to the determination for appropriateness in step S50 in FIG. 4 described hereinafter. Programs for carrying out various types of nuclear medicine diagnosis and arithmetic processes relating to the flows in FIGS. 4 and 5 described hereinafter are stored beforehand in a ROM. With the controller 5 executing the programs, the nuclear medicine diagnosis and arithmetic processes relating to the flows in FIGS. 4 and 5 according to the programs are carried out.

The reconstruction unit 12 and two-dimensional position map correcting unit 13 are realized by the controller 5 executing, for example, a program stored in the ROM of the storage medium represented by the above memory unit 8, or the commands inputted with a pointing device represented by the input unit 6.

The scintillator blocks 31 (see FIGS. 2 and 3) of the γ-ray detectors 3 convert into light the γ-rays generating from the patient M medicated with a radioactive drug. The photomultiplier tubes (PMT) 32 (see FIGS. 2 and 3) of the γ-ray detectors 3 multiply the converted light and convert it into electric signals. The electric signals are fed to the position calculating circuit 9 as image information (pixel values, i.e. a count of coincidences counted by the γ-ray detectors 3).

The position calculating circuit 9 refers to the look-up table 10 and refers to the two-dimensional position map at a time of nuclear medicine diagnosis, and determines which scintillator elements of the scintillator blocks 31 (see FIGS. 2 and 3) the count has occurred from. Specifically, incident positions on the scintillator elements are determined from a centroid calculation carried out at every incidence. The incident positions and counts (image information) obtained are fed to the coincidence circuit 11.

Specifically, when the patient M is medicated with a radioactive drug, two γ-rays are generated by annihilation of positrons of positron emission type RI. The coincidence circuit 11 checks positions of the scintillator blocks 31 (see FIGS. 2 and 3) (more particularly, positions of incidence on the scintillator elements) and incidence timing of the γ-rays, and determines received image information to be proper data only when the γ-rays are incident on two scintillator blocks 31 at opposite sides of the patient M at the same time. The coincidence circuit 11 ignores γ-rays incident only on one scintillator block 31.

Image information fed to the coincidence circuit 11 is fed as projection data to the reconstruction unit 12. The reconstruction unit 12 reconstructs the projection data to obtain images of the patient M. The images are fed to the output unit 7 through the controller 5. In this way, nuclear medicine diagnosis is carried out based on the images obtained by the reconstruction unit 12.

A γ-ray detector 3, as shown in FIGS. 2 and 3, includes a scintillator block 31 formed of a plurality of scintillator elements, and a photomultiplier tube (hereinafter abbreviated simply as "PMT") 32 optically coupled to the scintillator block 31. Each scintillator element forming the scintillator block 31 emits light with incidence of a γ-ray, thereby converting the γ-ray into light. The scintillator element detects the γ-ray by this conversion. The light emitted from the scintillator elements is fully diffused in the scintillator block 31, and is inputted to the PMT 32. The PMT 32 multiplies the light converted by the scintillator block 31, and converts it into electric signals. The electric signals are fed as image information (pixel values) to the position calculating circuit 9 (see FIG. 1) and also to the coincidence circuit 11 (see FIG. 1) as described above. The scintillator elements forming the scintillator block 31 correspond to the scintillator elements in this invention. The photomultiplier tube (PMT) 32 corresponds to the light sensor in this invention.

As shown in FIG. 3, one side of a scintillator element is set to $L_1$, the height of a scintillator element to $L_2$, the height of the scintillator block 31 to $L_3$, the width in the transverse direction of PMT 32 to $L_4$, the width in the longitudinal direction of PMT 32 to $L_5$, and the height of PMT 32 to $L_6$. This embodiment uses γ-ray detectors 3 of $L_1$=1.45 mm, $L_2$=4.5 mm, $L_3$=18 mm, $L_4$=52 mm, $L_5$=49.5 mm, and $L_6$=12.4 mm. Of course, each size of the γ-ray detectors 3 is not limited to this. This embodiment uses γ-ray detectors 3 with the scintillator block 31 having scintillator elements arranged in 32×32×4 layers, and the PMT 32 with 16×16 multi-anodes. There is no limitation as to the number of scintillator elements forming the scintillator block 31 or the number of multi-anodes of PMT 32.

Figure 4:
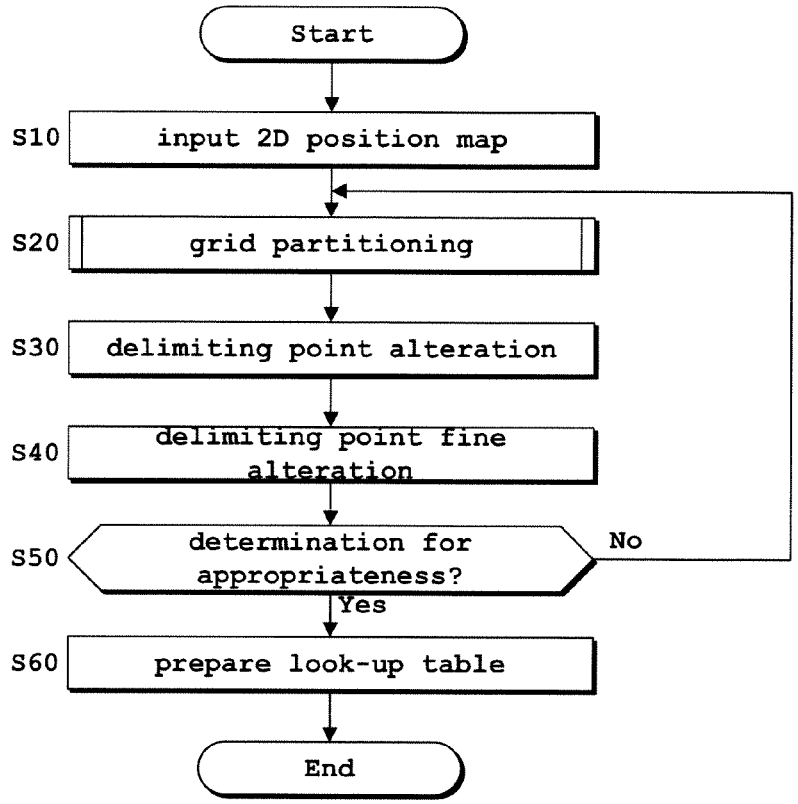
FIG. 4 is a flow chart showing arithmetic processes by a two-dimensional position map correcting unit.
Figure 5:
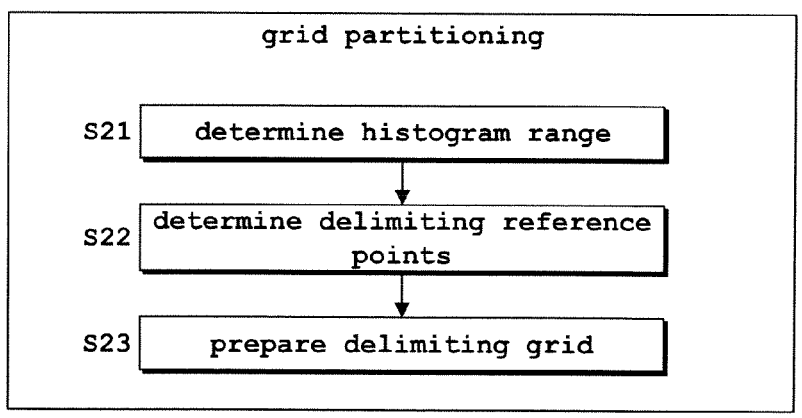
FIG. 5 is a flow chart showing arithmetic processes of grid partitioning in FIG. 4.
Figure 6:
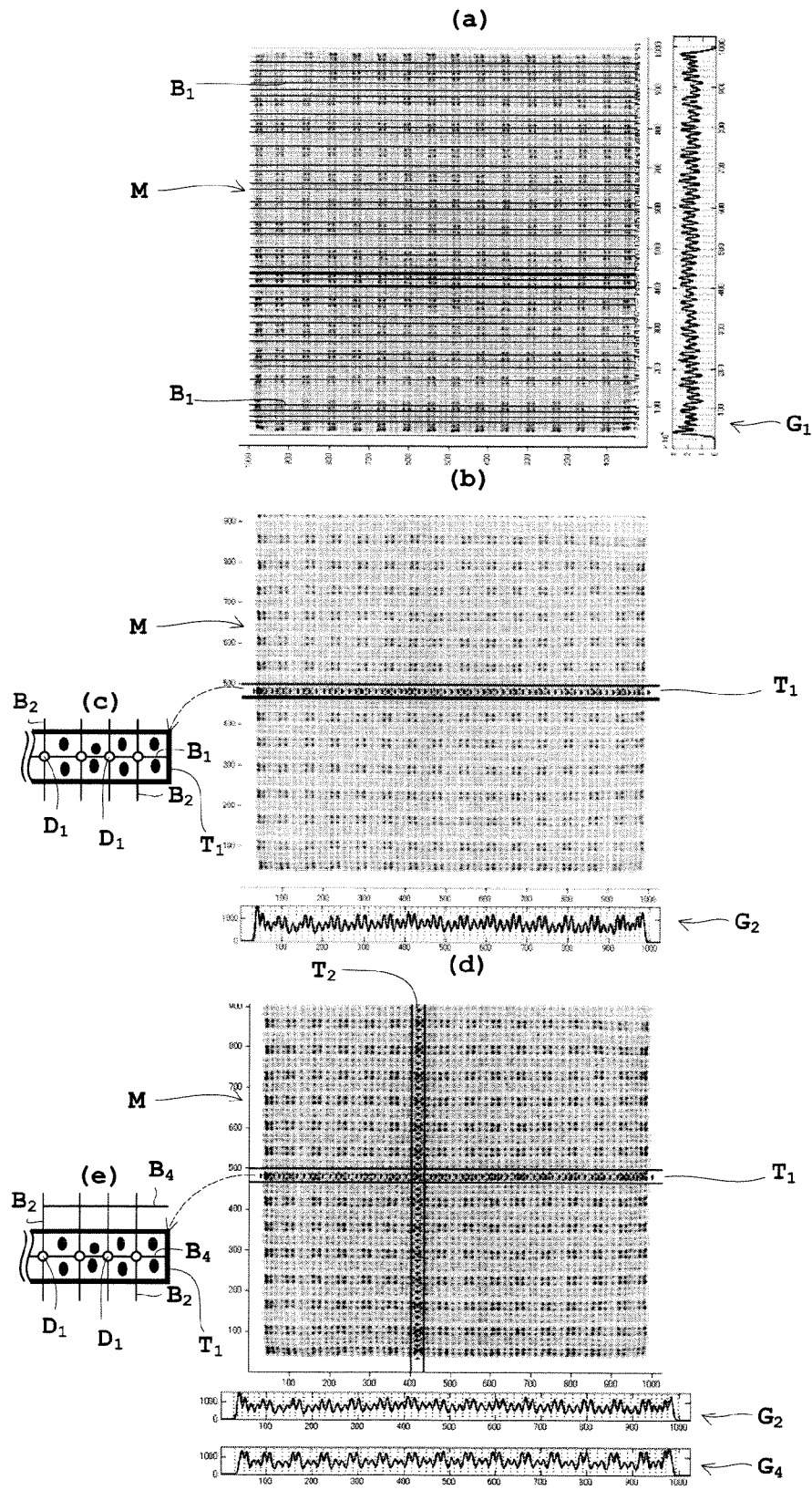
FIG. 6 is a plan view of the two-dimensional position map for use in description of the grid partitioning in FIGS. 4 and 5.
Figure 7:
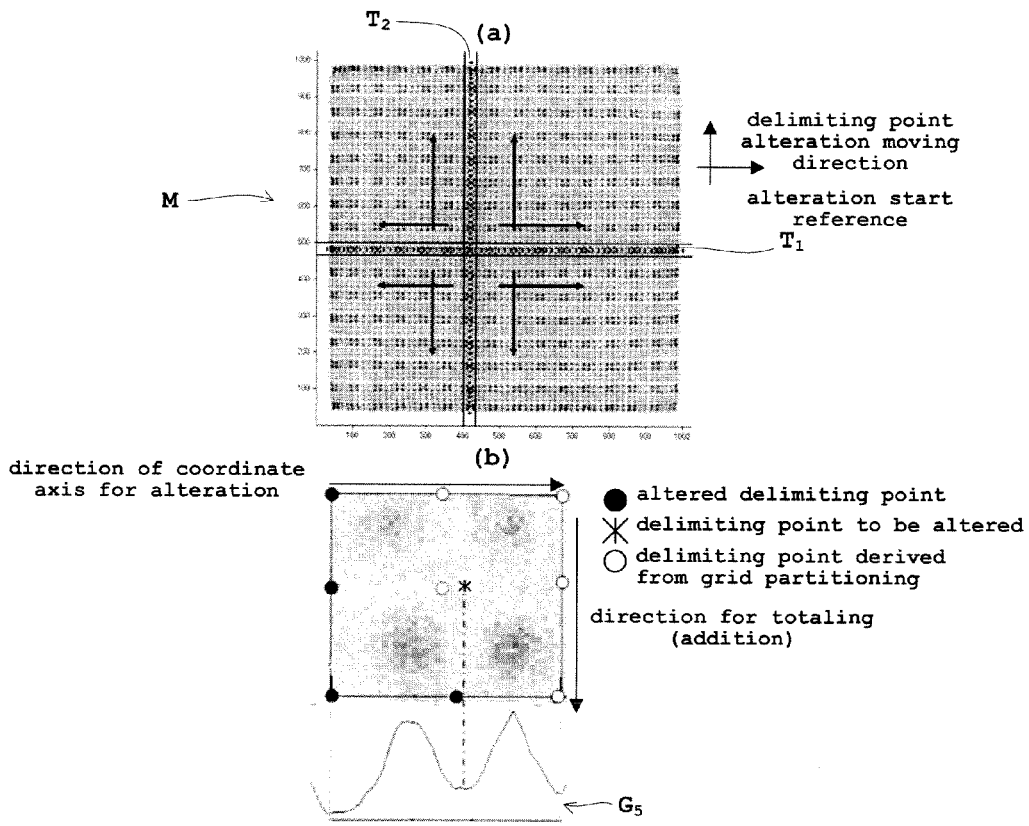
FIG. 7 is a plan view of the two-dimensional position map for use in description of delimiting point alteration in FIG. 4.
Figure 8:
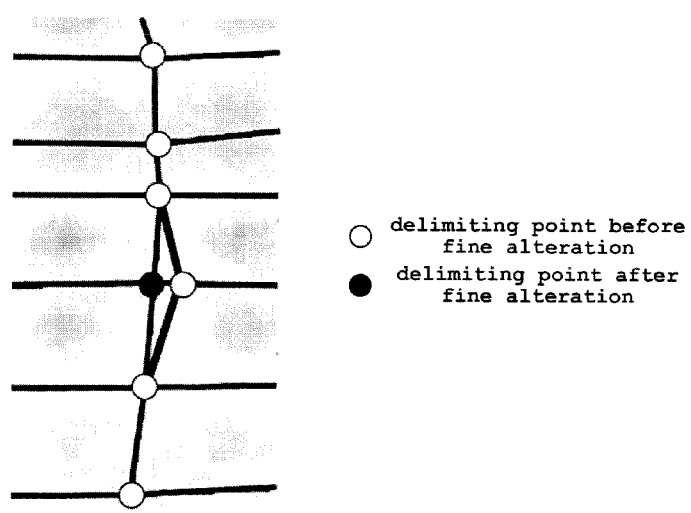
FIG. 8 is a plan view of the two-dimensional position map for use in description of delimiting point fine alteration in FIG. 4.

Next, arithmetic processes by the two-dimensional position map correcting unit 13 will be described with reference to FIGS. 4-8. FIG. 4 is a flow chart showing the arithmetic processes by the two-dimensional position map correcting unit. FIG. 5 is a flow chart showing arithmetic processes of grid partitioning in FIG. 4. FIG. 6 is a plan view of the two-dimensional position map for use in description of the grid partitioning in FIGS. 4 and 5. FIG. 7 is a plan view of the two-dimensional position map for use in description of delimiting point alteration in FIG. 4. FIG. 8 is a plan view of the two-dimensional position map for use in description of delimiting point fine alteration in FIG. 4.

(Step S10) Input Two-Dimensional Position Map

A two-dimensional position map is inputted (see FIG. 10). Specifically, after an Na-22 radiation source carries out uniform irradiation from above the γ-ray detectors 3 to obtain a two-dimensional position map and before carrying out an actual nuclear medicine diagnosis, a table is prepared by carrying out area division and labeling the entire map with location numbers of the scintillator elements, and is written and stored in the look-up table 10. In this embodiment, the two-dimensional position map is an image of 1024×1024 pixels, and the look-up table (LUT) has location numbers of the scintillator elements in the arrangement of 1024×1024. That is, on the look-up table (LUT), the respective positions (1024×1024 pixels) in the two-dimensional position map and the respective scintillator elements are in correspondence to one another.

(Step S20) Grid Partitioning

Grid partitioning is carried out after the two-dimensional position map is inputted in step 10.

(Step S21) Determine Histogram Range

Specifically, in order to determine a histogram range, totals of count values along the coordinate axes of the two-dimensional position map are obtained. As shown in FIG. 6 (a), for example, totals of count values along the direction of the coordinate axis relating to the rows of the two-dimensional position map M are obtained, respectively. At this time, for a portion where count values overlap, or when a count value is shared by two areas, because of an insufficient area division, the overlapping count values may both be added, and the count value shared by two areas may be added to one of them. A portion where count values overlap, or a count value being shared by two areas, is the case of distortion, or the case of an end area of the two-dimensional position map M. Preferably, therefore, totals of count values along the rows and columns except for those areas may be obtained.

As shown in FIG. 6 (a), when totals of count values along the direction of the coordinate axis relating to the rows of the two-dimensional position map M have been obtained, respectively, a histogram (graph) $G_1$ is acquired by preparing the histogram with a vertical axis representing the totals of count values and with a horizontal axis being the coordinate axis (i.e. the coordinate axis relating to the columns here) perpendicular to that coordinate axis (i.e. the coordinate axis relating to the rows here). The respective count values of the histogram $G_1$ are compared to determine respective local minimal values. In this embodiment, positions of these local minimal values are made delimiting points serving as provisional references, i.e. "provisional delimiting reference points". At these provisional delimiting reference points, straight parallel lines are drawn along the coordinate axis (in this case, the coordinate axis relating to the rows) on the two-dimensional position map M, to divide the two-dimensional position map M into a plurality of belts. These straight lines are termed boundaries $B_1$ in FIG. 6 (a).

And a total of count values at each boundary $B_1$ is obtained. In this embodiment, for every two adjacent belts including the belts divided by this boundary $B_1$, a total of the count values of the pixels included in the area of these two belts is obtained. For each belt divided by this boundary $B_1$, a total of the count values of the pixels included in the area of this one belt may be obtained.

When a total of the count values of the pixels included in the area of the two belts has been obtained, one area (in this embodiment, it is called "histogram range") serving as a reference is set based on that total. In this embodiment, when a total of the count values of the pixels included in the area of the two belts has been obtained, the total of the count values is compared with totals of the count values in other areas, and areas having the largest and the second largest totals are determined to be count ranges. The largest and second largest areas are selected in case the data of the largest itself is in error. Of course, only the largest area may be determined as the histogram range. End areas and areas with large belt widths and highly influenced by distortion on the two-dimensional position map M are excluded. The area (histogram range) delimited by the provisional delimiting reference points is termed reference area $T_1$ in FIG. 6 (b).

As is clear from the above description, this step S21 corresponds to the histogram preparing step in this invention, the histogram range determining step in this invention, and the provisional delimiting reference point determining step in this invention.

(Step S22) Determine Delimiting Reference Points

When reference area $T_1$ (histogram range) has been determined in step S21, the count values in the area $T_1$ (histogram range) which includes the largest and second largest areas are compared to obtain local minimal values, respectively. In this embodiment, positions of these local minimal values are made delimiting points serving as references, i.e. "delimiting reference points". That is, the count values in the area $T_1$ delimited at the provisional delimiting reference points determined in step S21 are compared to obtain local minimal values, respectively, and positions of these local minimal values are determined to be delimiting reference points. Specifically, when reference area $T_1$ (histogram range) has been determined, a graph $G_2$ is prepared, with a horizontal axis representing the area $T_1$ along the rows and a vertical axis representing the totals of count values. And points having the local minimal values in the graph $G_2$ are selected as delimiting reference points. These delimiting reference points are termed delimiting reference points $D_1$ in FIG. 6 (c) which is an enlargement of a portion of FIG. 6 (b). This step S22 corresponds to the delimiting reference point determining step in this invention. Steps 21 and step S22 described above constitute the delimiting point determining step in this invention.

(Step S23) Prepare Delimiting Grid

When delimiting reference points $D_1$ have been determined in step S22, respective boundaries $B_1$ are redrawn along the respective delimiting reference points $D_1$. Specifically, boundaries are redrawn along the columns perpendicular to the boundaries $B_1$ drawn along the rows. By this redrawing, a delimiting grid is formed on the two-dimensional position map M, thereby carrying out grid partitioning consisting of steps S21-S23. These redrawn boundaries are termed boundaries $B_2$ in FIG. 6 (c).

Thus, in FIGS. 6 (a)-6 (c), totals of the count values are obtained, respectively, along the direction of the coordinate axis relating to the rows of the two-dimensional position map M, and the histogram (graph) $G_1$ is obtained, with the vertical axis representing the totals (sums) of count values, and the horizontal axis being the coordinate axis relating to the columns which is perpendicular to the coordinate axis relating to the rows. The positions of the local minimal values in the histogram $G_1$ are determined to be provisional delimiting reference points. At these provisional delimiting reference points, parallel boundaries $B_1$ are drawn along the coordinate axis relating to the rows on the two-dimensional position map M. A total of the count values of the respective pixels included in the areas divided by each boundary $B_1$ is obtained to set the area $T_1$ along the rows. The graph $G_2$ is prepared, with the horizontal axis representing the area $T_1$ along the rows and the vertical axis representing the totals of count values. The positions of the local minimal values in the graph $G_2$ are determined to be delimiting reference points $D_1$. The boundaries $B_2$ are redrawn along the respective delimiting reference points $D_1$ and along the columns to prepare a delimiting grid along the direction of the columns, thereby carrying out grid partitioning in the direction of the columns. Similarly, the same procedure may be followed to carry out grid partitioning along the direction of the rows.

That is, totals of the count values are obtained, respectively, along the direction of the coordinate axis relating to the columns of the two-dimensional position map M, and a histogram (graph) $G_3$ (not shown in FIG. 6) is acquired, with a vertical axis representing the totals (sums) of count values, and a horizontal axis being the coordinate axis relating to the rows which is perpendicular to the coordinate axis relating to the columns. The positions of the local minimal values in the histogram $G_3$ are determined to be provisional delimiting reference points. At these provisional delimiting reference points, parallel boundaries $B_3$ (not shown in FIG. 6) are drawn along the coordinate axis relating to the columns on the two-dimensional position map M. A total of the count values of the respective pixels included in the areas divided by each boundary $B_3$ is obtained to set an area $T_2$ along the columns (see FIG. 6 (d)). A graph $G_4$ (see FIG. 6 (d)) is prepared, with a horizontal axis representing the area $T_3$ along the columns and a vertical axis representing the totals of count values. The positions of the local minimal values in the graph $G_4$ are determined to be delimiting reference points $D_2$ (not shown in FIG. 6). Boundaries $B_4$ (see FIG. 6 (e)) are redrawn along the respective delimiting reference points $D_2$ and along the rows to prepare a delimiting grid along the direction of the rows, thereby carrying out grid partitioning in the direction of the rows.

The grid partitioning along the direction of the columns (steps S21-S23) and the grid partitioning along the direction of the rows (steps S21-S23) may be carried out in parallel. The grid partitioning along the direction of the rows (steps S21-S23) may be carried out after the grid partitioning along the direction of the columns (steps S21-S23). Conversely, the grid partitioning along the direction of the columns (steps S21-S23) may be carried out after the grid partitioning along the direction of the rows (steps S21-S23).

(Step S30) Delimiting Point Alteration

The positions of delimiting points to be altered are altered by comparing respective count values around the delimiting points to be altered, while successively and contiguously moving from one to another of the boundaries $B_2$ and $B_4$ redrawn in step S23, with reference to the areas $T_1$ and $T_2$ set in step S21. In this embodiment, the area where the areas $T_1$ and $T_2$ cross each other is the alteration start reference. This alteration start reference is the reference point which is the delimiting reference point $D_1$ and also the delimiting reference point $D_2$. From this alteration start reference, alteration is made in the direction of each coordinate axis along the directions of arrows in FIG. 7 ($a$) (delimiting point alteration moving directions). This alteration is carried out for successive adjacent boundaries $B_2$ and $B_4$, in other words, while moving from one to another of adjacent delimiting points, thereby altering all the delimiting points.

As shown in FIG. 7 ($b$), for example, in altering the delimiting points, a partial total graph $G_5$ with a horizontal axis representing the direction of the coordinate axis for alteration and a vertical axis representing the total (sum) of the count values added in a direction normal to the coordinate axis is obtained for an area surrounded by eight delimiting points around a delimiting point to be altered. Each boundary is redrawn based on the partial total graph $G_5$ which is an alteration result. The black dots ("•" in FIG. 7) indicate altered delimiting points, the asterisk ("*" in FIG. 7) indicates the delimiting point to be altered, and the white circles ("○" in FIG. 7) indicate delimiting points derived from the grid partitioning. The position of the delimiting point is altered by regarding the position coordinates of a local minimal value derived from the partial total graph $G_5$ as altered coordinates of the delimiting point. This step S30 corresponds to the altering step in this invention.

(Step S40) Delimiting Point Fine Alteration

The positions of the delimiting points are re-altered by comparing the respective delimiting points altered in step S30. This re-alteration is smaller than the alteration in step S30, and is therefore defined as "fine alteration" in this specification. This embodiment obtains absolute values of differences (hereinafter referred to simply as "difference values") between the coordinates of delimiting points adjacent each other in the direction of the coordinate axis for alteration, and obtains an average value of the difference values of the delimiting points remaining after excluding one delimiting point having the largest increment of coordinates. Next, it is determined for each delimiting point whether a sum of difference values to the adjacent delimiting points corresponds at least to predetermined times (e.g. four times) the average value of the difference values. When the sum of difference values to the adjacent delimiting points corresponds at least to the predetermined times the average value of the difference values, that delimiting point is determined to be an outstanding point with discontinuity. Conversely, when the sum of difference values to the adjacent delimiting points is less than the predetermined times the average value of the difference values, that delimiting point is determined not to stand out but to maintain continuity. And when determined to be discontinuous, the position of the delimiting point is fine-altered by making the average value of the coordinates of the adjacent delimiting points the coordinates after fine alteration.

The white circles ("○" in FIG. 8) indicate delimiting points before the fine alteration, and the black dot ("•" in FIG. 8) a delimiting point after the fine alteration. It will be seen that the first to third upper white circles and the first and second white circles from the bottom in FIG. 8 maintain continuity, and that only the third white circle from the bottom stands out with discontinuity. Then, the delimiting point of the third white circle from the bottom can be re-altered to the position of the delimiting point of the black dot by fine alteration. Based on the delimiting point indicated by the black dot reflecting the re-alteration result, each boundary is redrawn as shown in FIG. 8.

As is clear from the above description, this step S40 corresponds to the delimiting point re-altering step in this invention.

(Step S50) Determination for Appropriateness?

Determination as to appropriateness is carried out by applying map determination conditions using amounts of characteristic extracted from grid shapes delimited vertically and horizontally on the two-dimensional position map, to the results of area division (the areas $T_1$ and $T_2$ reflecting also the alteration in step S30 and the fine alteration in step S40) delimited at the delimiting points fine-altered (re-altered) in step S40 as described above.

The map determination conditions are stored beforehand in the memory unit 8 (see FIG. 1). As the map determination conditions, the following conditions are cited, for example.

A. A ratio between of an average width of the grid near the left end and an average width of the grid near the right end is a predetermined ratio or less.

B. A ratio between of an average width of the grid near the upper end and an average width of the grid near the lower end is a predetermined ratio or less.

C. Grids with horizontal to vertical ratios of the width deviating from 1 exist in a predetermined number or less.

D. An average size near ends of the grid is smaller than an average size in the center.

Determination may be made for appropriateness when any one of these conditions is satisfied. A plurality of these conditions may be combined, and determination may be made for appropriateness when all the conditions combined are satisfied.

Condition A and condition B indicate that a ratio between an average width at one end and an average width at the other end of the grid delimited at the delimiting points is a predetermined ratio or less. If the ratio between the average widths exceeds the predetermined ratio, it can be considered that the difference in width between the ends has increased, and thus these areas can be determined inappropriate. Conversely, if the ratio between the average widths is the predetermined ratio or less, it can be considered that there is little difference in width between the ends, and thus these areas can be determined appropriate. There is no particular limitation here as to a specific value of the predetermined ratio, but it may be set as appropriate according to design matter. For example, when the difference in width between the ends exceeding 1.5 times—twice renders the areas inappropriate, the predetermined ratio can be set to 1.5 times—twice.

Condition C indicates that grids with horizontal to vertical ratios of the width of the grids delimited at the delimiting points deviating from 1 exist in a predetermined number or less. The closer to 1 the horizontal to vertical ratio of the width of the grid is, the closer the grid is to a square. Conversely, the farther it deviates from 1, the farther away the grid is from a square. Therefore, if grids deviating from 1 exceed the predetermined number, such area can be determined inappropriate. Conversely, if grids deviating from 1 exist in the predetermined number or less, such area can be determined appropriate. There is no particular limitation as to a specific value of the horizontal to vertical ratio of the width of the grid deviating from 1, but it may be set as appropriate according to design matter. For example, a grid is counted as deviating from 1 when the horizontal to vertical ratio exceeding 1.5 times—twice. Similarly, there is no particular limitation as to the predetermined number, but it may be set as appropriate according to design matter. For example, when the number exceeding 1/256 of the whole renders the area inappropriate, the number can be set to 1/256 of the whole (in the case of areas $T_1$ and $T_2$, 8 which corresponds to 1/256 of 2×1024).

Figure 9:
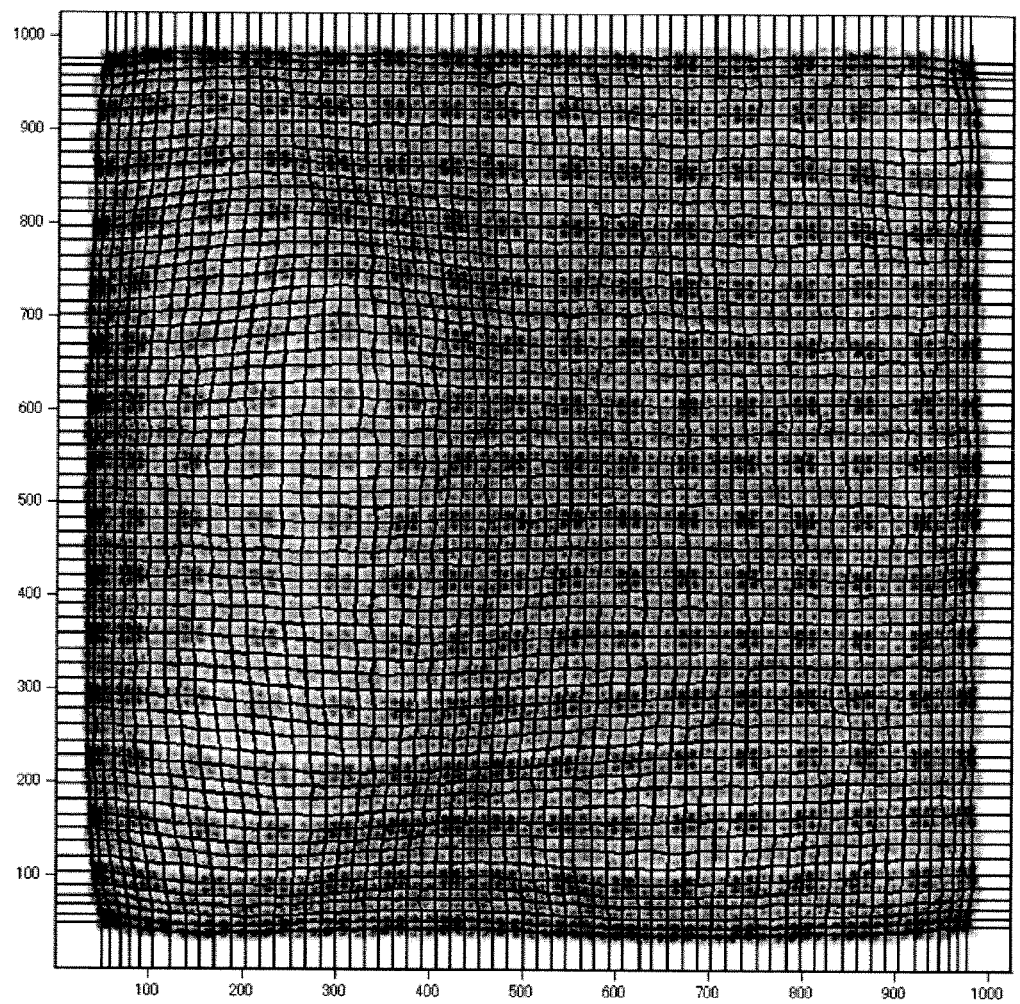
FIG. 9 is a plan view showing an example of area discrimination of the two-dimensional position map which is a correction result.

Condition D indicates that an average size near an end is smaller than an average size in the center of the grid delimited at the delimiting points. When the size near an end of the grid is larger than the size in the center, as shown in a left area of FIG. 9, for example, the grid at the end is squeezed by the grid near the end, and thus such area can be determined inappropriate. Conversely, when the size near the end of the grid is smaller than the size in the center, the grid at the end is not squeezed by the grid near the end, and thus such area can be determined appropriate. There is no particular limitation as to nearness to the end, but a setting may be made as appropriate according to design matter. For example, when the center area is set to 0 among areas from the end to the center, an area of 1/4-7/8 can be set as near the end as shown in FIG. 9. The same applies to the right area, upper area and lower area in FIG. 9.

When the above map determination conditions are satisfied (that is, in the case of determination for appropriateness) with respect to the areas $T_1$ and $T_2$, the areas $T_1$ and $T_2$ are regarded as inappropriate, and the operation moves to next step S60 for preparing a look-up table as a final result of this area division. When the above map determination conditions are not satisfied with respect to the areas $T_1$ and $T_2$, the areas $T_1$ and $T_2$ are regarded as appropriate, and the operation returns to S21 of step S20, in which areas having the third and fourth largest totals of count values of the pixels included in the areas of the two belts partitioned by the provisional delimiting reference points are set as histogram range, and similarly, steps S22 and S23 and steps S30, S40 and S50 are repeated. Thereafter, similarly, until the map determination condition is satisfied, the areas delimited by the delimiting points (provisional delimiting reference points in this embodiment) are changed in the order of large total of the count values, and step S50 (including steps S22 and S23 and steps S30 and S40) is repeated.

The correction may be stopped when the number of times of repeating step S50 exceeds a preset number of times. The correction may be stopped when the areas delimited by the delimiting points no longer exist in step S50. Through such determination, a failure in dividing the areas can be determined automatically. There is no particular limitation as to the preset number of times also, but it may be set as appropriate according to design matter.

As is clear from the above description, this step S50 corresponds to the map determining step in this invention.

(Step S60) Prepare Look-Up Table

Through the above steps S10-S50 (including also steps S21-S23), the two-dimensional position map correcting unit 13 reads the two-dimensional position map from the look-up table 10 and, by rewriting and correcting it, prepares a look-up table.

FIG. 9 shows a plan view showing an example of area discrimination of the two-dimensional position map which is a correction result. FIG. 9 shows a case where the arrangement of scintillator element areas has distortion (there is distortion in areas leftward from the center in FIG. 9). It is confirmed in FIG. 9 also that, even when there is such distortion, discrimination can be made by correcting the two-dimensional position map. Further, it is confirmed in FIG. 9 also that, by redrawing boundaries to make alteration and fine alteration (re-alteration), the boundaries are redrawn in the areas with distortion, and grid partitioning is carried out as divided by the redrawn boundaries.

According to the two-dimensional position map correcting method carried out with the PET apparatus in this embodiment having the construction described hereinbefore, a histogram preparing step (step S21) is provided for acquiring a histogram by preparing the histogram with a vertical axis representing count values of the two-dimensional position map and with a horizontal axis being in a coordinate axis direction of the two-dimensional position map. A map determining step (step S50) is provided for applying a map determination condition using amounts of characteristic extracted from grid shapes delimited vertically and horizontally on the two-dimensional position map, to areas delimited by delimiting points (provisional delimiting reference points in this embodiment) based on the histogram acquired in the histogram preparing step (step S21). Even when the areas delimited by the delimiting points are not appropriate and the area division has failed, success or failure of area division in such areas can easily be determined by applying the map determination condition in the map determining step (step S50). And since the areas delimited by the delimiting points (provisional delimiting reference points in this embodiment) are changed and the map determining step (step S50) is repeated until the map determination condition is satisfied, the areas satisfying the map determination condition are determined appropriate and the area division in such areas can be carried out accurately. Even when there is distortion, the two-dimensional position map can be corrected accurately.

In this embodiment, totals of the count values are obtained along a coordinate axis of the two-dimensional position map, and the above histogram (e.g. histogram $G_1$) is acquired by preparing the histogram with a vertical axis representing the totals of the count values and with a horizontal axis being in a coordinate axis perpendicular to that coordinate axis.

In this embodiment, the map determining step is repeated by applying the above map determination condition to the areas delimited by the delimiting points (provisional delimiting reference points in this embodiment), and changing the areas delimited by the delimiting points in the order of large total of the count values until the map determination condition is satisfied. Normally, areas with large totals of the count values are regarded as appropriate. When the map determination condition is not satisfied, the areas concerned are regarded as inappropriate, and the areas are changed in the order of large total of the count values, and the map determining step (step S50) is repeated, whereby an area with the largest total of the count values can be found among the areas regarded as appropriate.

In order to find the above delimiting points, preferably, a delimiting point determining step (steps S21 and S22) is provided for comparing the respective count values of the histogram, and obtaining local minimum values, respectively, thereby to determine positions of the local minimum values to be the delimiting points. By obtaining the local minimum values, the respective delimiting points (provisional delimiting reference points and delimiting reference points in this embodiment) can be determined accurately.

In this embodiment, preferably, the delimiting point determining step (steps S21 and S22) includes a provisional delimiting reference point determining step (step S21) for determining delimiting points serving as provisional references to be provisional delimiting reference points, and a delimiting reference point determining step (step S22) for comparing the respective count values in the areas divided at the provisional delimiting reference points determined in the provisional delimiting reference point determining step (step S21), and obtaining the local minimum values, respectively, thereby to determine positions of these local minimum values to be reference delimiting points which are delimiting points serving as references. In this case, after determining the provisional delimiting reference points, the reference points are determined.

In this embodiment, preferably, a delimiting point altering step (step S30) is provided for altering the positions of the delimiting points to be altered, based on the delimiting reference points determined in the above delimiting reference point determining step (step S22), by comparing respective count values around the delimiting points to be altered. After alterations made in the delimiting point altering step (step S30), the map determination condition is applied in step S50. With this alteration of the delimiting points, the altered delimiting points have distortion taken into account, and the areas delimited by the delimiting points will also become accurate.

In this embodiment, preferably, a delimiting point re-altering step (step S40) is provided for re-altering (fine-altering) the positions of the delimiting points by comparing the respective delimiting points altered in the above delimiting point altering step (step S30). After the re-alteration (fine alteration) made in the delimiting point re-altering step (step S40), the map determination condition is applied in step S50. With this re-alteration (fine alteration) of the delimiting points, the re-altered (fine-altered) delimiting points have distortion taken into account still further, and the areas delimited by the delimiting points will also become still more accurate.

This invention is not limited to the foregoing embodiment, but may be modified as follows:

(1) In the foregoing embodiment, a PET apparatus has been described as an example of nuclear medicine diagnostic apparatus having the radiation detecting apparatus. This invention is applicable also to a SPECT (Single Photon Emission CT) apparatus which detects a single γ-ray to reconstruct a sectional image of a patient. It is applicable also to a PET-CT apparatus which is a combination of a PET apparatus and a CT apparatus. It is applicable also to radiation other than γ (e.g. α-rays, β-rays and so on).

(2) The foregoing embodiment provides DOI detectors each having of a plurality of scintillator elements arranged in three dimensions. The invention is applicable also to radiation detectors each having a plurality of scintillator elements arranged in two dimensions or three dimensions.

(3) In the foregoing embodiment, the photomultiplier tubes (PMT) have been described as an example of light sensors. There is no limitation as long as light sensors are optically coupled to the scintillator elements, as exemplified by avalanche photodiodes and silicon photomultipliers.

(4) The foregoing embodiment has employed count values as signal strengths. However, electric signals having continuous values may be employed as signal strengths.

(5) In the foregoing embodiment, local minimal values are obtained to determine positions of the local minimum values to be delimiting points (provisional delimiting reference points and delimiting reference points in this embodiment). Local maximal values may be employed instead. However, when count values are employed as signal strengths as in the foregoing embodiment, it is more desirable to employ local minimal values as in the embodiment since the boundaries of the two-dimensional position map correspond to portions of the local minimal values.

(6) In the foregoing embodiment, the map determination conditions noted hereinbefore are applied to the areas delimited by the delimiting points, and until the map determination conditions are satisfied, the areas delimited by the delimiting points are changed in the order of large total of the signal strengths (count values in the foregoing embodiment), and the map determining step (step S50) is repeated. However, it is not absolutely necessary to change in the order of large total of the signal strengths (count values in the foregoing embodiment). The map determining step may be repeated after changing in the order of areas adjoining the largest and second largest areas.

(7) In the foregoing embodiment, the delimiting point determining step includes the provisional delimiting reference point determining step (step S21) for determining delimiting points serving as provisional reference to be provisional delimiting reference points, and the delimiting reference point determining step (step S22) for comparing the respective signal strengths (count values in the foregoing embodiment) in the areas divided at the provisional delimiting reference points determined in the provisional delimiting reference point determining step (step S21), and obtaining the local minimum values, respectively, thereby to determine positions of these local minimum values to be delimiting points. However, it is not absolutely necessary to take the provisional delimiting reference point determining step. That is, only the delimiting reference points may be determined, without determining the provisional delimiting reference points.

(8) The foregoing embodiment provides the delimiting point altering step (step S30) for altering positions of the delimiting points to be altered, and the delimiting point re-altering step (step S40) for re-altering (fine-altering) the positions of the delimiting points. However, it is not absolutely necessary to carry out the alteration and the re-alteration (fine alteration) after the alteration. Only the alteration may be made: it is unnecessary to make both the alteration and re-alteration.

(9) In the foregoing embodiment, the map determination conditions are conditions A-D. However, these are not limitative, but may be other conditions using amounts of characteristic extracted from the grid shapes delimited vertically and horizontally on the two-dimensional position map.

The invention claimed is:

1. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:

a histogram preparing step for acquiring a histogram by preparing the histogram with a vertical axis representing signal strengths of the two-dimensional position map and with a horizontal axis being in a coordinate axis direction of the two-dimensional position map; and a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points, wherein the map determining step is repeated by applying the map determination condition to the areas delimited by the delimiting points, and changing the areas delimited by the delimiting points in the order of large total of the signal strengths until the map determination condition is satisfied.

2. The two-dimensional position map correcting method according to claim 1, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

3. The two-dimensional position map correcting method according to claim 1, wherein correction is stopped when the number of times of repeating the map determining step exceeds a preset number of times.

4. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:

a histogram preparing step for acquiring a histogram by preparing the histogram with a vertical axis representing signal strengths of the two-dimensional position map and with a horizontal axis being in a coordinate axis direction of the two-dimensional position map; and a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points, wherein correction is stopped when the areas delimited by the delimiting points no longer exist in the map determining step.

5. The two-dimensional position map correcting method according to claim 4, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

6. The two-dimensional position map correcting method according to claim 4, wherein correction is stopped when the number of times of repeating the map determining step exceeds a preset number of times.

7. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:

a histogram preparing step for acquiring a histogram by preparing the histogram with a vertical axis representing signal strengths of the two-dimensional position map and with a horizontal axis being in a coordinate axis direction of the two-dimensional position map;

a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points; and a delimiting point determining step for comparing the respective signal strengths of the histogram, and obtaining local minimum values, respectively, thereby to determine positions of these local minimum values to be the delimiting points, wherein the delimiting point determining step is a delimiting reference point determining step for determining delimiting points serving as references to be reference delimiting points, the two-dimensional position map correcting method further comprises a delimiting point altering step for altering the positions of the delimiting points to be altered, based on the delimiting reference points determined in the delimiting reference point determining step, by comparing respective signal strengths around the delimiting points to be altered, and after alterations made in the delimiting point altering step, the map determination condition is applied.

8. The two-dimensional position map correcting method according to claim 7, comprising:

a delimiting point re-altering step for re-altering the positions of the delimiting points by comparing the respective delimiting points altered in the delimiting point altering step;

wherein, after re-alterations made in the delimiting point re-altering step, the map determination condition is applied.

9. The two-dimensional position map correcting method according to claim 7, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

10. The two-dimensional position map correcting method according to claim 7, wherein correction is stopped when the number of times of repeating the map determining step exceeds a preset number of times.

11. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:

a histogram preparing step for acquiring a histogram by preparing the histogram with a vertical axis representing signal strengths of the two-dimensional position map and with a horizontal axis being in a coordinate axis direction of the two-dimensional position map;

a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points; and a delimiting point determining step for comparing the respective signal strengths of the histogram, and obtaining local minimum values, respectively, thereby to determine positions of these local minimum values to be the delimiting points, wherein the delimiting point determining step includes:

a provisional delimiting reference point determining step for determining delimiting points serving as provisional references to be provisional reference delimiting points; and a delimiting reference point determining step for comparing the respective signal strengths in the areas divided at the provisional delimiting reference points determined in the provisional delimiting reference point determining step, and obtaining the local minimum values, respectively, thereby to determine positions of these local minimum values to be reference delimiting points which are delimiting points serving as references, the two-dimensional position map correcting method further comprises a delimiting point altering step for altering the positions of the delimiting points to be altered, based on the delimiting reference points determined in the delimiting reference point determining step, by comparing respective signal strengths around the delimiting points to be altered, and after alterations made in the delimiting point altering step, the map determination condition is applied.

12. The two-dimensional position map correcting method according to claim 11, comprising:

a histogram range determining step for drawing boundaries in form of straight parallel lines along a coordinate axis of the two-dimensional position map, at the provisional reference delimiting points determined in the provisional delimiting reference point determining step, to divide the two-dimensional position map into a plurality of belts, obtaining a total of signal strengths at each of the boundaries, comparing totals of signal strengths in the respective belts, and determining an area having the largest or second largest total to be a histogram range serving as a reference;

wherein the delimiting reference point determining step is executed to compare signal strengths in the histogram range determined in histogram range determining step to obtain local minimum values, respectively, thereby to determine positions of these local minimum values to be the reference delimiting points.

13. The two-dimensional position map correcting method according to claim 11, comprising:

a delimiting point re-altering step for re-altering the positions of the delimiting points by comparing the respective delimiting points altered in the delimiting point altering step;

wherein, after re-alterations made in the delimiting point re-altering step, the map determination condition is applied.

14. The two-dimensional position map correcting method according to claim 11, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

15. The two-dimensional position map correcting method according to claim 11, wherein correction is stopped when the number of times of repeating the map determining step exceeds a preset number of times.

16. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:

a histogram preparing step for acquiring a histogram by preparing the histogram with a vertical axis representing signal strengths of the two-dimensional position map and with a horizontal axis being in a coordinate axis direction of the two-dimensional position map; and a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points, wherein the map determination condition is that a ratio between an average width at one end and an average width at the other end of the grid delimited at the delimiting points is a predetermined ratio or less.

17. The two-dimensional position map correcting method according to claim 16, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

18. The two-dimensional position map correcting method according to claim 16, wherein correction is stopped when the number of times of repeating the map determining step exceeds a preset number of times.

19. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:
- a histogram preparing step for acquiring a histogram by preparing the histogram with a vertical axis representing signal strengths of the two-dimensional position map and with a horizontal axis being in a coordinate axis direction of the two-dimensional position map; and
- a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points,
- wherein the map determination condition is that grids with horizontal to vertical ratios of the width of the grids delimited at the delimiting points deviating from 1 exist in a predetermined number or less.

20. The two-dimensional position map correcting method according to claim 19, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

21. The two-dimensional position map correcting method according to claim 19, wherein correction is stopped when the number of times of repeating the map determining step exceeds a preset number of times.

22. A two-dimensional position map correcting method used when detecting radiation with radiation detectors each formed of a plurality of scintillator elements arranged in one dimension, two dimensions or three dimensions, and a light sensor optically coupled thereto, for preparing a look-up table from a two-dimensional position map presenting, in two dimensions, signal strengths obtained with the light sensor as corresponding to incident positions of the radiation incident on the scintillator elements, the two-dimensional position map correcting method comprising:
- a histogram preparing step for acquiring a histogram by preparing the histogram with a vertical axis representing signal strengths of the two-dimensional position map and with a horizontal axis being in a coordinate axis direction of the two-dimensional position map; and
- a map determining step for applying a map determination condition using amounts of characteristic extracted from grid shapes delimited vertically and horizontally on the two-dimensional position map, to areas delimited by delimiting points based on the histogram acquired in the histogram preparing step, the map determining step being repeated until the map determination condition is satisfied, by changing the areas delimited by the delimiting points,
- wherein the map determination condition is that an average size near an end is smaller than an average size in a center of the grid delimited at the delimiting points.

23. The two-dimensional position map correcting method according to claim 22, wherein the histogram preparing step is executed to obtain totals of the signal strengths along a coordinate axis of the two-dimensional position map, and acquire the histogram by preparing the histogram with a vertical axis representing the totals of the signal strengths and with a horizontal axis being in a coordinate axis perpendicular to that coordinate axis.

24. The two-dimensional position map correcting method according to claim 22, wherein correction is stopped when the number of times of repeating the map determining step exceeds a preset number of times.

* * * * *